United States Patent [19]

Kelman

[11] Patent Number: 4,601,722

[45] Date of Patent: * Jul. 22, 1986

[54] INTRAOCULAR LENS

[76] Inventor: Charles D. Kelman, North Shore Towers, 269 Grand Central Pkwy., Bldg. 3, Floral Park, N.Y. 11005

[*] Notice: The portion of the term of this patent subsequent to Jun. 5, 2001 has been disclaimed.

[21] Appl. No.: 666,335

[22] Filed: Oct. 30, 1984

[51] Int. Cl.⁴ .............................................. A61F 2/16
[52] U.S. Cl. ........................................................ 623/6
[58] Field of Search ............................................ 623/6

[56] References Cited

U.S. PATENT DOCUMENTS 4,172,297 10/1979 Schlegel .................................. 623/6
4,298,996 11/1981 Barnet ..................................... 623/6
4,451,938 6/1985 Kelman ................................... 623/6
4,535,488 8/1985 Haddad ................................... 623/6

Primary Examiner—Richard J. Apley
Assistant Examiner—James Prizant
Attorney, Agent, or Firm—Henry Sternberg; Bert J. Lewen

[57] ABSTRACT

An intraocular lens which may be inserted into the eye through an incision in the cornea which is substantially less than 5 mm in length. The lens includes a lens body which comprises a plurality of lens body portions and magnet means for assembly of the lens body portions within the eye after they are individually inserted through the incision.

25 Claims, 8 Drawing Figures

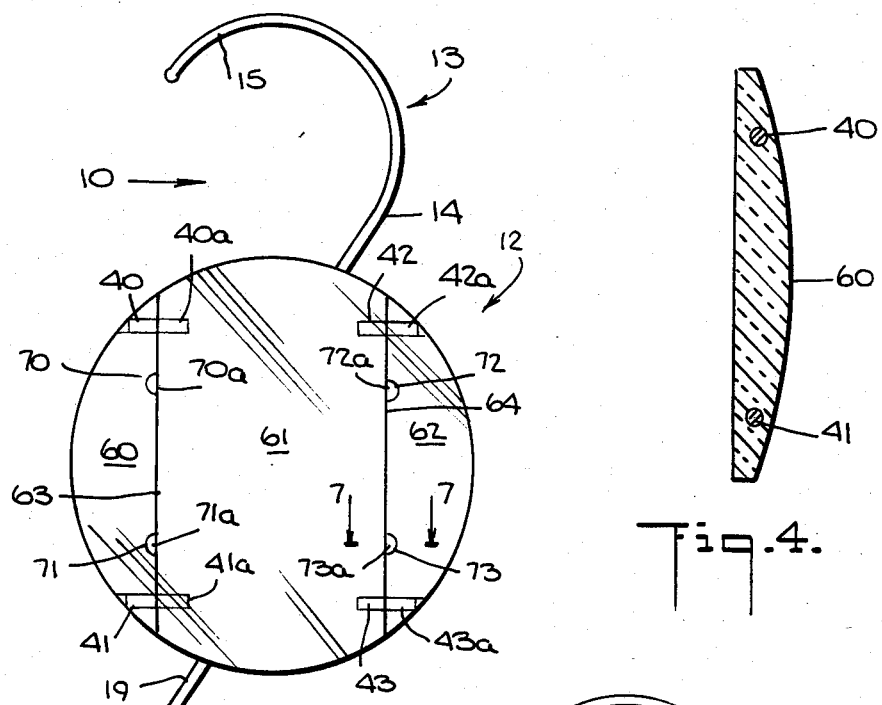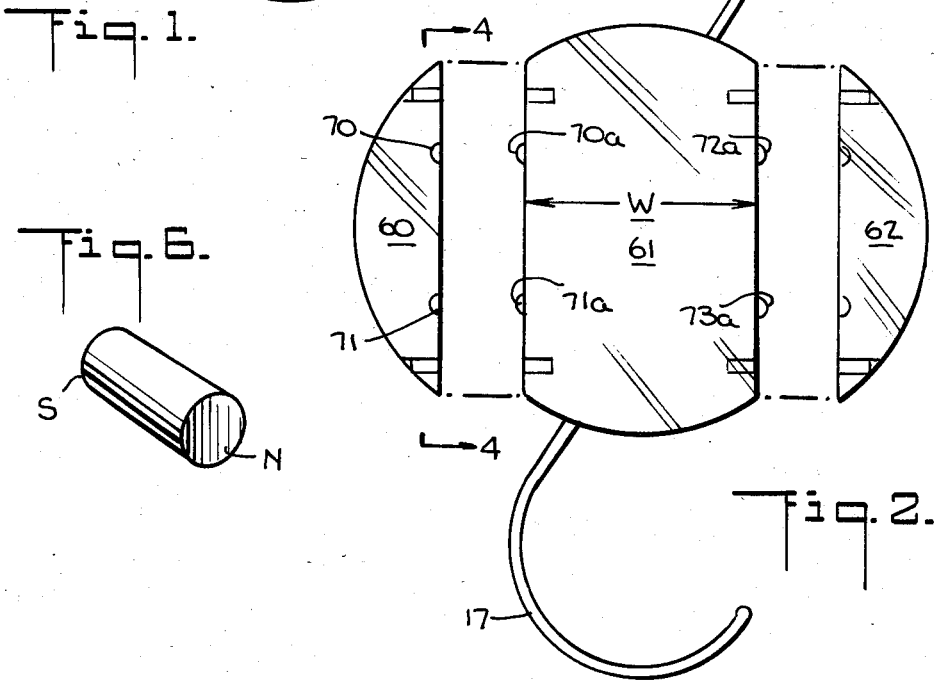

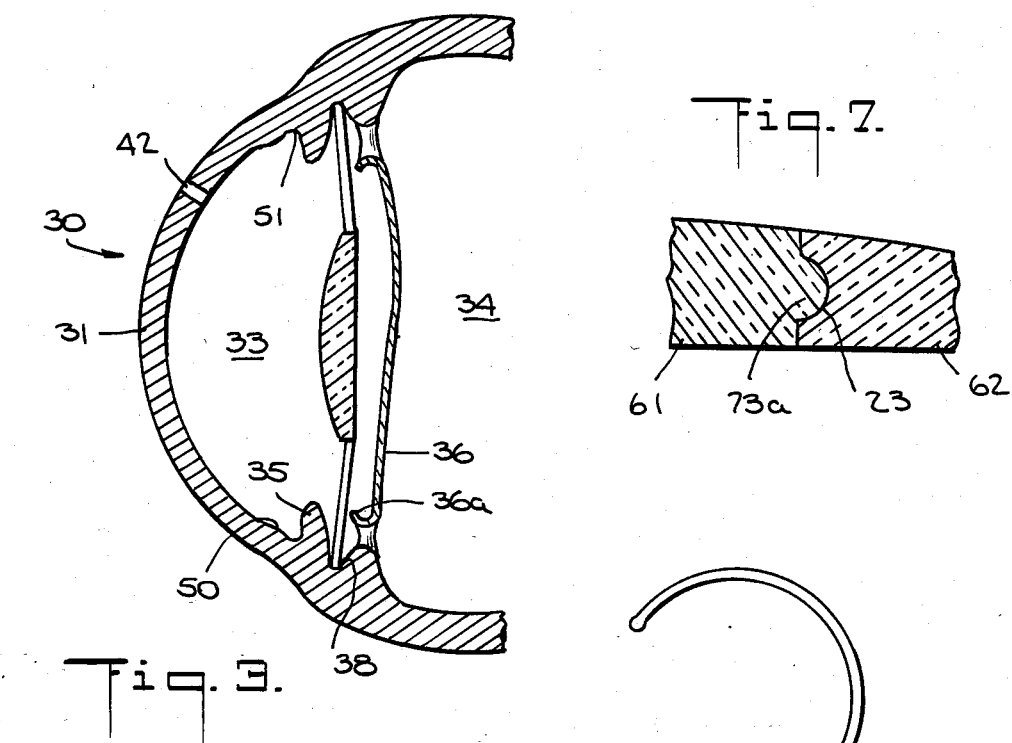
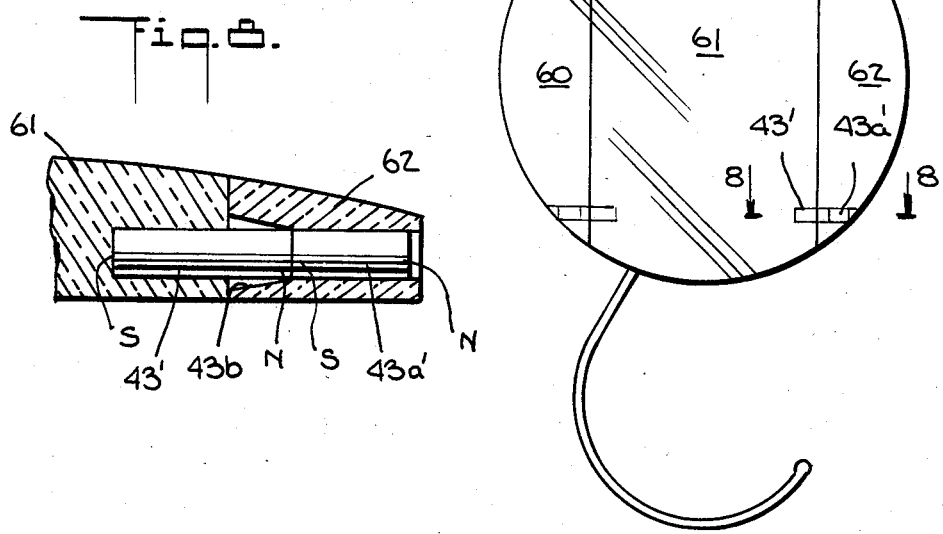

INTRAOCULAR LENS

BACKGROUND OF THE INVENTION

The present invention relates to an intraocular lens which is adapted to be seated in the eye, for example, in the anterior chamber, the posterior chamber or partly in the anterior chamber and partly in the posterior chamber, after the removal of a natural lens.

It has been found that the insertion of an introcular lens is by far the best solution to correcting vision after cataract surgery. The proper implanation of an intraocular lens always involves the risk of damage to the eye particularly during the insertion process as well as at a later time if the intraocular lens dislocates or must be removed or replaced.

To place the lens in the eye, the surgeon ordinarily makes an incision or opening in the cornea which aligns with the pupil, and the surgeon passes the lens through the opening. The position-fixation members of the lens are flexible and can be bent to pass through the opening. Accordingly, the minimum length of the opening which must be made is ordinarily determined by the diameter of the lens body, or optic, which ordinarily has a circular periphery and which is substantially rigid, being formed of a material such as, for example, polymethylmethacrylate and having a configuration which provides the desired optical characteristics. It is, of course, desirable to make the opening in the cornea as small as possible to minimize the risk of damage to the eye.

In my copending patent application Ser. Nos. 575,018 and 612,584 are disclosed lenses which I have developed which utilize a miniature optic, for example an optic which is only about 3 mm in diameter, in conjunction with a frame or side members which are opaque, so as to prevent the glare which would otherwise result from use of such miniature optic alone.

SUMMARY OF THE INVENTION

It is an object of the present invention, therefore, to provide a new and improved intraocular lens which avoids one or more of the disadvantages of prior such lenses.

It is another object of the invention to provide a new and improved intraocular lens which can be inserted into the eye through a smaller opening than was heretofore required.

It is another object of the invention to provide a new and improved lens body for an intraocular lens, which lens body can be inserted into the eye through a smaller opening than was heretofore required.

In accordance with the invention, an intraocular lens comprises a medial light-focussing lens body comprised of a plurality of detachably connected portions each of which individually exhibits a dimension substantially smaller than the minimum length dimension of the opening in the eye which would be required for insertion therethrough of the assembled lens body so that such individual portions can be inserted into the eye, when the lens body is disassembled, through a smaller opening in the eye than the opening through which the lens body as a whole could be inserted when assembled. The lens body includes magnet means on said portions for detachably connecting said portions to each other and is capable of being assembled within the eye after insertion of the individual portions into the eye. The lens also includes position-fixation means extending from different peripheral regions of the lens body and adapted to seat within an eye for fixing the position of the lens body within the eye.

In accordance with one embodiment of the invention, the plurality of separable portions are a central optic portion for focusing light and a pair of substantially opaque side portions for preventing glare. The optic portion is of miniature size, i.e. having a dimension which permits its insertion through an opening in the eye substantially smaller than 5 mm in length.

Also in accordance with the invention, a lens body for an intraocular lens and adapted for insertion into the eye through an opening therein comprises a plurality of separate portions held in an initial relation by a magnet means connecting the plurality of portions. The lens body portions may be individually inserted into the eye through said opening therein and may be assembled together within the eye. The magnet means is capable of holding the plurality of portions substantially in their initial relation after they are assembled together.

For a better understanding of the present invention, together with other and further objects thereof, reference is made to the following description taken in connection with the accompanying drawings, and its scope will be pointed out in the appended claims.

BRIEF DESCRIPTION OF THE DRAWINGS

FIG. 1 is a plan view of an embodiment of the present invention intended for fixation in, for example, the posterior chamber of the eye;

FIG. 2 is a plan view of the FIG. 1 lens with the individual lens body portions thereof separated prior to insertion in the eye;

FIG. 3 is a side elevational view of the FIG. 1 lens fixed within an eye, shown in section;

FIG. 4 is a side elevational view of the lens body of the present invention taken along line 4—4 of FIG. 2;

FIG. 5 is a plan view of a lens body according to another embodiment of the present invention;

FIG. 6 is an enlarged, perspective view of a magnet member according to one embodiment of the present invention;

FIG. 7 is a fragmentary, enlarged view taken along line 7—7 of FIG. 1; and

FIG. 8 is a fragmentary, enlarged view taken along line 8—8 of FIG. 5.

DESCRIPTION OF THE PREFERRED EMBODIMENTS

With reference to the drawings, the invention as a whole is depicted in the figures and denoted by reference character 10. The intraocular lens structure 10 includes as one of its elements a medial lens body 12, FIG. 1. The lens body 12 includes a light focusing central portion 61 which may be constructed of any biologically inert, transparent material suitable for optical correction such as, for example, polymethylmethacrylate and a pair of side portions 60 and 62 which may be constructed of the same or any other biologically inert material but which are substantially opaque.

Lens structure 10 is intended for insertion and fixation within an eye 30, after cataract removal. Eye 30 includes a cornea 31, an anterior chamber 33, a posterior chamber 34 and an iris 35. FIG. 3 shows eye 30 after an extracapsular surgical procedure in which, after the natural lens has been removed, the posterior capsule 36, as well as a small part of anterior capsule 36a remains. Ciliary sulcus 38 of the posterior chamber is located between the sulcus of capsule 36, 36a and the iris 35.

A pair of position fixation members 13, 17 are connected with the lens body 12 and extend from different peripheral regions of the lens body and are adapted to seat within an eye for fixing the position of the lens body within the eye. First position fixation member 13 has a first portion 14 contiguous to and extending generally laterally outwardly from a first region of the periphery of the lens body 12. First position fixation member 13 has a second portion 15 extending from the end of the first portion 14 generally transversely thereto and at least partly peripherally of the lens body 12 to provide support for the lens in, for example, the posterior chamber of the eye.

As seen in FIG. 1 lens structure 10 includes also a second position fixation member 17. Second member 17 includes a first portion 19 extending generally laterally outwardly from a second region of the periphery of the lens body 12 spaced from the first region and in direction generally opposite to that of the first position fixation member 13 for extending to the periphery of the iris and a second portion 20, similar to portion 15 for seating in, for example, the ciliary sulcus 38 of the eye as represented in FIG. 3.

First and second position fixation members 13, 17 may be molded integrally with lens body 12 or connected thereto by an adhesive, ultrasonic welding, fusion, or any other connection method known in the art. It should be noted that first and second position fixation members 13, 17 are also preferably constructed of biologically inert and nonabsorbative material such as polymethylmethacrylate, and the like. Preferably the first and second members 13, 17 are resilient, or springy and have a memory, such that they will tend to return toward the position shown in FIG. 1 after compression or extension away from the represented configuration.

According to the preferred embodiment of the invention, the lens body has a substantially circular periphery and has a plurality of separate portions, for example, three portions 60, 61, 62, in an initial relation preferably separated by a pair of parallel cluts 63, 64, along chord lines extending longitudinally across the lens body 12 from one peripheral region to the opposite peripheral region thereof.

Embedded in the central optic portion 61, in the region of the edges formed by cuts 63, 64 are a plurality of magnets 40a, 41a on one side and 42a, 43a on the other side. The magnets may be rod shaped as seen in FIG. 6 and may be of the type known as JOBMAX 18 "ultra high energy Magnets" sold by the Jobmaster Corporation 9010 Liberty Road, of Randallstown, Md. Such magnets are made of Samarium Colbalt Alloy in the form of rods about 1 mm long and ½ mm in diameter.

Embedded in each of the side portions 60 and 62, along the edges thereof formed by the cuts 63 and 64, each in axial alignment with the corresponding one of the respective magnets 40a, 41a and 42a, 43a, are magnets 40, 41, 42, and 43. Each of the magnets in the side portions is oriented with its magnet poles opposite to the magnetic orientation of the corresponding one of the magnets in the central optic portion so that a magnetic force of attraction will exist therebetween. Thus for example, the north pole of magnet 40 will face the south pole of the corresponding adjacent magnet 40a. Each of the two outer portions 60, 62 of the lens body may have a plurality of lateral apertures, for example, 70, 71, or 72, 73 therein, respectively, adapted to receive small lateral projections 70a, 71a, 72a and 73a respectively which project across the cuts 63, 64 for locating the three lens body portions 60, 61, 62 in a desired fixed relation to one another, which preferably is substantially their initial relation as represented in FIG. 1.

Alternatively to having projections 70, 71, 72 and 73, each of the magnets of the central portion 61 may, according to another embodiment of the invention, seen in FIG. 5, be positioned so as to project across the respective cuts 63, 64 into a corresponding lateral aperture in portions 60, 62 for maintaining the three lens body portions 60, 61, 62 in substantially their initial relation, as represented in FIG. 3, when the lens is seated in the eye. In this embodiment the magnets 40a, 41a, 42a and 43a of the central optic portion 61 extend laterally outwardly from the edges of the central optic portion toward the respective outer portion 60, 62 into a corresponding aperture in the outer portions, whereby the magnets themselves form the projections for locating the desired relation between the three lens portions.

Referring now to FIGS. 5 and 8 of the drawings, it will be seen that in this embodiment, the rod shaped magnets, e.g., member 43a, projects laterally from the central lens body into a preferably conical aperture 43b in the adjacent side portion 62 and that this apenture contains the opposed magnet 43a of opposite polarity so that the two magnets will attract one another.

From the foregoing description, it will be seen that an intraocular lens 10 in accordance with the invention comprises a multi-component lens body 12 which can be disassembled so that the widest portion thereof will not exceed a dimension w, as represented in FIG. 2, which is smaller than the maximum dimension d of the lens body 12 when assembled, as represented in FIG. 1, so that the lens body 12 can be inserted into the eye, when the lens body 12 is disassembled, through a smaller opening in the eye than the opening through which the assembled lens body 12 could be inserted.

The lens body 12 preferably has a circular periphery with a diameter of, for example, 6 mm. The elongated central portion 61 preferably has a height of about 6 mm, which permits more light to pass through when the pupil is dilated, as e.g. at night. The opaque outer portions on the otherhand, inhibit the passage of light therethrough thus reducing the possibility of glare at the edges formed by the cuts 63, 64. Such glare would otherwise result from the 5-6 mm diameter bundle of light rays normally passing through the pupil and impinging on the cuts 63, 64 which, due to the miniature size of the optic, are spaced only about 3 mm apart.

Since the position-fixation members 13, 17 can be flexed and/or snaked through an opening in the eye of less than 2 mm. the "w" dimension of the central portion of the lens body, which in accordance with the present invention is preferably of the order of magnitude of 3 mm will control the minimum size incision required. Accordingly an incision of only about 3 mm will be required.

In order to place the lens 10 in the eye through an incision 42 made by the surgeon in the cornea 31, the surgeon disassembles the lens body as represented in FIG. 2.

After the central portion 61 has been inserted through incision 42, one of the pair of side portions 60, 62 is inserted, and, once in the eye, is assembled to the central portion by the surgeon stabilizing such central portion with one instrument while with a second instrument bringing the side portion into magnetic engagement therewith. The same procedure is then followed for assembly of the second side portion of the lens body to the central portion thereof.

It will be understood that one instrument may be inserted by the surgeon through the incision 42 in the eye (FIG. 2) while a second instrument may be inserted by the surgeon through a second very small incision which is ordinarily made in the eye for other purposes. Using two instruments at the same time the surgeon can attach the three lens body portions to each other inside the eye as described.

From the foregoing description it will be apparent that a lens constructed in accordance with the invention can be inserted into an eye through a smaller incision than the diameter of the conventional lens body, thereby minimizing the risk of damage to the eye and can be readily assembled and disassembled within the eye, without the need for sutures or other additional assembled parts.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens comprising:
   a lens body comprised of a plurality of individual portions;
   magnet means on said plurality of portions for detachably connecting said plurality of portions;
   whereby said plurality of portions can be individually inserted into the eye and assembled together therein into said lens body; and
   position fixation means extending from said lens body and adapted to seat within an eye for fixing the position of said lens body within the eye.

2. A lens in accordance with claim 1 in which said lens body has three portions separated by a pair of substantially parallel cuts extending longitudinally across said lens body, said magnet means on said lens body connecting said three portions of said lens body.

3. A lens in accordance with claim 2 in which said three portions of said lens body comprise a central portion and two outer portions and in which said magnet means comprises a plurality of magnet members. one another when the lens is seated in the eye.

4. A lens in accordance with claim 3 in which each of said two outer portions of said lens body has at least one of said magnets embedded therein.

5. A lens body for an intraocular lens and adapted for insertion into the eye through an opening therein which is substantially less than 5 mm in length comprising:
   a plurality of separate portions in an initial relation; and
   magnet means on said lens body detachably connecting said plurality of portions, said magnet means being capable of maintaining said plurality of portions substantially in their initial relation upon positioning of said plurality of portions in such relation to one another.

6. A lens body in accordance with claim 5 in which said lens body has three portions separated by a pair of substantially parallel cuts along chord lines extending longitudinally across said lens body, said lens body having said magnet means positioned on opposite sides of each said cuts of said lens body for connecting together said three portions of said lens body.

7. A lens body in accordance with claim 6 in which said three portions of said lens body comprise a central portion and two outer portions and in which said magnet means is located at the edges of said central and said outer portions respectively which are in abutment when the lens body is in assembled condition.

8. A lens body in accordance with claim 7 in which each of said two outer portions of said lens body has an edge portion, and part of said magnet means is a magnet member embedded in the region of said edge portion and adapted to cooperate with a corresponding magnet member embedded in said central portion for maintaining said three lens portions in a desired fixed relation to one another when the lens is seated in the eye.

9. A lens body in accordance with claim 8 further comprising locating means at each of said edges respectively, for maintaining said three lens body portions in substantially their initial relation to one another when the lens is seated in the eye.

10. A lens body in accordance with claim 5 in which said magnet means are formed of Samarium Cobalt Alloy.

11. A lens body in accordance with claim 10 comprising position fixation means for supporting said lens body within the eye.

12. An intralocular lens according to claim 1, wherein said central portion is adapted to focus rays of light and each of said side portions is substantially opaque to light.

13. An intraocular lens according to claim 3, wherein said central optic portion is substantially rigid and has a maximum dimension, transverse to the direction of its insertion into an eye, which is substantially less than 5 mm in length so that said central optic portion can be inserted through an opening in the cornea which is substantially less than 5 mm in length.

14. An intraocular lens according to claim 13, wherein said outer portions are each substantially rigid and each has a maximum dimension, transverse to the direction of its insertion into an eye, which is substantially less than 5 mm in length so that said outer portions can each be inserted through an opening in the cornea which is substantially less than 5 mm in length.

15. An intraocular lens according to claim 3, wherein said central optic portion and said outer portions are all made of the same material, said central portion having an optical finish and said outer portions having a rough unground surface resulting in their being opaque.

16. An intraocular lens according to claim 3, wherein each said magnet members is rod-shaped, and have a length of about 1 mm and a diameter of about ½ mm.

17. An intraocular lens according to claim 16, wherein said magnet members are formed of Samarium Cobalt Alloy.

18. An intraocular lens according to claim 1, wherein said central optic portion has a generally rectangular configuration.

19. An intraocular lens according to claim 18, further comprising locating means on said central portion and on each said outer portions for locating the latter with respect to said central portion for facilitating assembly thereof within the eye.

20. An intraocular lens according to claim 19, wherein said locating means comprises a projection on one of said lens portions and a corresponding aperture on the adjacent one of said lens portion.

21. An intraocular lens according to claim 16, wherein at least one of said magnet members protrudes outwardly from an edge of one of said portions and the adjacent edge of the abutting one of said portions comprises an aperture for receiving said protruding magnet member for locating the portions in question with respect to each other.

22. An intraocular lens according to claim 18, wherein said central optic portion has a height to width relation of about 2:1.

23. An intraocular lens comprising:
a lens body having a miniature central lightfocusing optic portion and a pair of separate substantially opaque outer portions adapted to be located adjacent to opposite peripheral regions of said central optic portion;
first magnet means at said opposite peripheral regions of said miniature central optic portion;
second magnet means on each said outer portions of said lens body for cooperating with said first magnet means on said central optic portion for detachably connecting said outer portions with said central optic portion, whereby said central optic portion and said opaque outer portions can each be independently inserted into the eye, through a smaller opening in the eye than the opening through which said lens body could be inserted after it is assembled; and
position-fixation means cooperating with at least one of said portions for fixing the position of said lens body within the eye.

24. An intraocular lens according to claim 23 wherein said central optic portion has substantially straight edges defining said opposite peripheral regions thereof and each said opaque outer portion has a straight edge adapted to closely abut against a corresponding one of said edges of said central portion.

25. An intraocular lens according to claim 24 wherein said central optic portion is generally rectangular in shape and said straight edges thereof define the elongated sides of such rectangle.

* * * * *

UNITED STATES PATENT AND TRADEMARK OFFICE
CERTIFICATE OF CORRECTION

PATENT NO. : 4,601,722
DATED : July 22, 1986
INVENTOR(S) : Charles D. Kelman

It is certified that error appears in the above—identified patent and that said Letters Patent are hereby corrected as shown below:

Claim 3, line 48, delete "one"; line 49, delete "another when the lens is seated in the eye.".

Signed and Sealed this

Seventh Day of October, 1986

[SEAL]

*Attest:*

DONALD J. QUIGG

*Attesting Officer*     *Commissioner of Patents and Trademarks*